US012564738B2

(12) United States Patent
Lee

(10) Patent No.: US 12,564,738 B2
(45) Date of Patent: Mar. 3, 2026

(54) TEMPERATURE MEASUREMENT-BASED HIGH-INTENSITY FOCUSED ULTRASOUND OUTPUT DEVICE

(71) Applicant: SKINGRAB CO., LTD., Seoul (KR)

(72) Inventor: Sugun Lee, Paju-si (KR)

(73) Assignee: SKINGRAB CO., LTD., Seoul (KR)

( * ) Notice: Subject to any disclaimer, the term of this patent is extended or adjusted under 35 U.S.C. 154(b) by 29 days.

(21) Appl. No.: 18/428,395

(22) Filed: Jan. 31, 2024

(65) Prior Publication Data

US 2024/0165431 A1 May 23, 2024

Related U.S. Application Data

(63) Continuation of application No. PCT/KR2022/011566, filed on Aug. 4, 2022.

(30) Foreign Application Priority Data

Aug. 5, 2021 (KR) ......................... 10-2021-0102831
Jul. 27, 2022 (KR) ......................... 10-2022-0093199

(51) Int. Cl.
*A61N 7/02* (2006.01)
*A61N 7/00* (2006.01)

(52) U.S. Cl.
CPC ........ *A61N 7/02* (2013.01); *A61N 2007/0091* (2013.01)

(58) Field of Classification Search
CPC .. A61N 7/02; A61N 2007/0091; A61N 7/022; A61N 2007/0034;
(Continued)

(56) References Cited

U.S. PATENT DOCUMENTS

2006/0149169 A1* 7/2006 Nunomura ............... A61N 7/00
601/2
2010/0204695 A1* 8/2010 Mehta ................ A61B 18/1206
606/42
(Continued)

FOREIGN PATENT DOCUMENTS

KR 10-0895358 B1 4/2009
KR 10-2012-0040909 A 4/2012
(Continued)

OTHER PUBLICATIONS

KR20120040909 Translation (Year: 2012).*
(Continued)

*Primary Examiner* — Adil Partap S Virk
(74) *Attorney, Agent, or Firm* — Studebaker Brackett PLLC

(57) ABSTRACT

The present invention relates to a temperature measurement-based high-intensity focused ultrasound output device comprising: a cartridge which has a head part to be brought into contact with a target region of the skin; a transducer which is provided in the cartridge to output ultrasound toward the target region; a temperature sensor which is provided in the head part to measure the temperature of the target region; and a controller which operates or stops the transducer on the basis of temperature data measured by the temperature sensor.

15 Claims, 8 Drawing Sheets

(58) Field of Classification Search
CPC ...... A61N 2007/0095; A61N 2007/025; A61B
2018/00791; A61B 2018/00875; A61B
5/00; A61B 5/01; A61B 5/0531; A61B
5/441
See application file for complete search history.

(56) References Cited

U.S. PATENT DOCUMENTS

| | | | | |
|---|---|---|---|---|
| 2015/0105701 A1* | 4/2015 | Mayer | ..................... | A61N 7/02 601/3 |
| 2015/0260691 A1* | 9/2015 | Nakayama | ............. | G01N 29/34 73/661 |
| 2020/0289089 A1* | 9/2020 | Nelson | ................... | A61B 5/282 |

FOREIGN PATENT DOCUMENTS

| | | | | | |
|---|---|---|---|---|---|
| KR | 20120040909 A | * | 4/2012 | .............. | A61N 7/02 |
| KR | 10-1562998 B1 | | 10/2015 | | |
| KR | 10-2016-0129826 A | | 11/2016 | | |
| KR | 20160129826 A | * | 11/2016 | ............. | A61B 18/14 |
| KR | 10-2016-0139516 A | | 12/2016 | | |
| KR | 10-2018-0014930 A | | 2/2018 | | |
| KR | 10-2143977 B1 | | 8/2020 | | |
| KR | 10-2021-0076820 A | | 6/2021 | | |
| KR | 20210076820 A | * | 6/2021 | .............. | A61N 7/02 |

OTHER PUBLICATIONS

KR20160129826 Translation (Year: 2016).*
"Notice of Preliminary Examination Result" Office Action issued in KR 10-2022-0093199; mailed by the Korean Intellectual Property Office on Nov. 14, 2022.
"Notice of Allowance" Office Action issued in KR 10-2022-0093199; mailed by the Korean Intellectual Property Office on Jan. 5, 2023.
International Search Report issued in PCT/KR2022/011566; mailed Nov. 14, 2022.

* cited by examiner

TEMPERATURE MEASUREMENT-BASED HIGH-INTENSITY FOCUSED ULTRASOUND OUTPUT DEVICE

CROSS-REFERENCE TO RELATED APPLICATIONS

The present application is a continuation of International Patent Application No. PCT/KR2022/011566, filed on Aug. 4, 2022, which is based upon and claims the benefit of priority to Korean Patent Application Nos. 10-2021-0102831 filed on Aug. 5, 2021 and 10-2022-0093199 filed on Jul. 27, 2022. The disclosures of the above-listed applications are hereby incorporated by reference herein in their entirety.

BACKGROUND

Embodiments of the present disclosure described herein relate to a temperature measurement-based high-intensity focused ultrasound output device.

Generally, an ultrasound output device focuses ultrasound on a target part of a skin without causing damage to a surface of the skin, thereby inducing coagulation necrosis in the target part. Thereafter, the target part of the necrotic skin may be naturally restored by a damaged part recovery mechanism of a human body.

An ultrasound output device according to the related art includes a handpiece disposed adjacent to a skin, a cartridge housing coupled to the handpiece, and a transducer that is provided in the cartridge housing and outputs a high-intensity focused ultrasound to the skin.

However, the ultrasound output device according to the related art transmits the same amount of ultrasound to each target part of the skin even though the amounts of transmitted ultrasound that causes the coagulation necrosis are different for each target part of the skin.

Thus, in the related art, there is a problem in that burns occur in the target part of the skin as the amount of ultrasound, which is greater than an appropriate amount, is transmitted to the target part of the skin, and there is a problem in that coagulation necrosis cannot be induced in the target part of the skin as the amount of ultrasound, which is smaller than an appropriate amount, is transmitted to the target part of the skin.

SUMMARY

Embodiments of the present disclosure provide a temperature measurement-based ultrasound output device that may transmit an appropriate amount of ultrasound to a target part of a skin as a transducer is operated or stopped according to a temperature measured at the target part of the skin while the transducer transmits ultrasound to the target part of the skin.

The aspects of the present disclosure are not limited to the aspects described above, and those skilled in the art will clearly understand other aspects not described from the following description.

According to an embodiment, a temperature measurement-based ultrasound output device includes a cartridge having a head part in contact with a target part of a skin, a transducer that is provided in the cartridge and outputs ultrasound toward the target part, a temperature sensor that is provided in the head part and measures a temperature at the target part, and a controller that operates or stops the transducer based on temperature data measured by the temperature sensor.

Further, the controller may operate the transducer when the temperature data measured by the temperature sensor is smaller than or equal to a set reference temperature value and stops the transducer when the temperature data is greater than the set reference temperature value.

Further, the temperature sensor may be provided in plurality, and the plurality of temperature sensors may be arranged symmetrically to the head part, and the controller may calculate an average value of the temperature data measured by the plurality of temperature sensors, operate the transducer when the average value is smaller than or equal to a set reference temperature value, and stop the transducer when the average value is greater than the set reference temperature value.

Further, the reference temperature value set by the controller may increase or decrease according to a focus depth of the ultrasound focused on the target part.

Further, the temperature measurement-based ultrasound output device may further include a high-frequency electrode that is provided in the head part, provides electrical energy to the target part, and measures an impedance at the target part, wherein the controller may operate the transducer when impedance data measured by the high-frequency electrode is smaller than or equal to a set reference impedance value and stop the transducer when the impedance data is greater than the set reference impedance value.

Further, the high-frequency electrode may be provided in plurality, and the plurality of high-frequency electrodes may be arranged symmetrically to the head part.

Further, the temperature measurement-based ultrasound output device may further include a handpiece detachably coupled to the cartridge, a connector protruding from the cartridge toward the headpiece, and a connector insertion part provided in the handpiece and detachably coupled to the connector.

Further, the temperature measurement-based ultrasound output device may further include a knob that supports the connector, is movably provided in the handpiece, and allows the connector to reciprocate such that the connector is positioned at a locked position in which the connector is locked to the connector insertion part or an unlocked position in which the connector is unlocked from the connector insertion part.

Further, the temperature measurement-based ultrasound output device may further include an elastic member that generates an elastic force to the knob such that the connector is positioned in the locked position.

Further, the temperature measurement-based ultrasound output device may further include a guide protrusion provided in the knob, and a guide groove that is provided in the handpiece such that the guide protrusion reciprocates and guides the knob so that the knob reciprocates between the locked position and the unlocked position.

The specific details of the present disclosure are included in the detailed description and the drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Advantages and features of the present disclosure and a method of achieving the advantages and the features will become apparent with reference to embodiments described below in detail in conjunction with the accompanying drawings. However, the present disclosure is not limited to the embodiments described below but may be implemented in various forms, and the present embodiments merely make the disclosure of the present disclosure complete and are provided to completely inform the scope of the present disclosure to those skilled in the art to which the present disclosure belongs, and the present disclosure is merely defined by the scope of the appended claims.

Unless otherwise defined, all the terms (including technical and scientific terms) used herein may be used as meanings that may be commonly understood by those skilled in the art to which the present disclosure belongs. Further, terms defined in a commonly used dictionary are not interpreted ideally or excessively unless explicitly and specifically defined.

Hereinafter, embodiments of the present disclosure will be described in detail with reference to the accompanying drawings.

Figure 1:
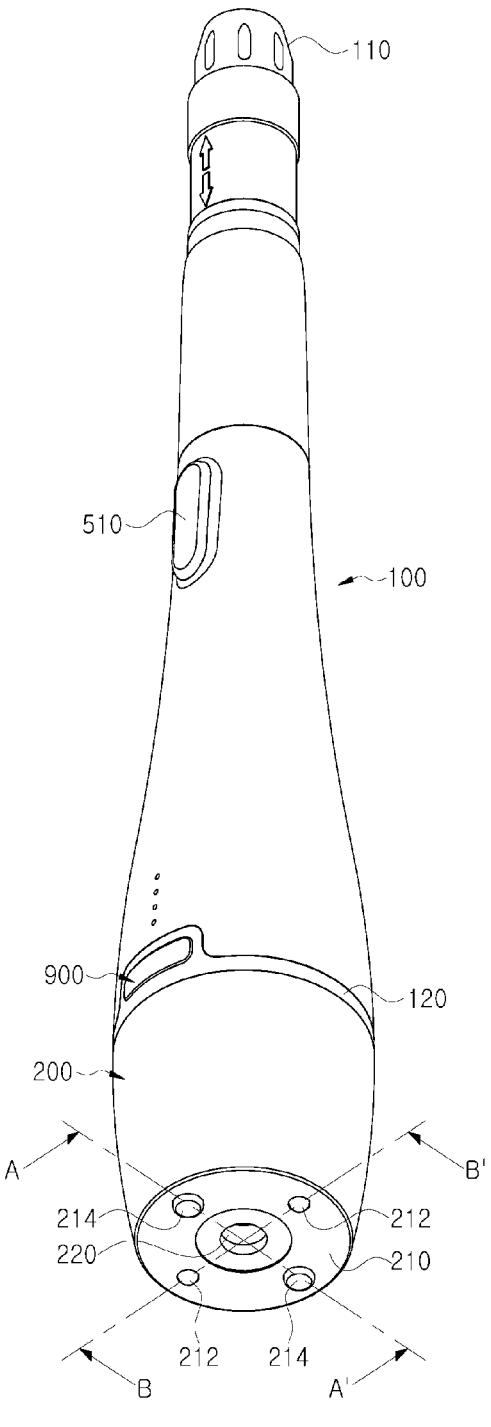
FIG. 1 is a perspective view illustrating a temperature measurement-based ultrasound output device according to an embodiment of the present disclosure.
Figure 2:
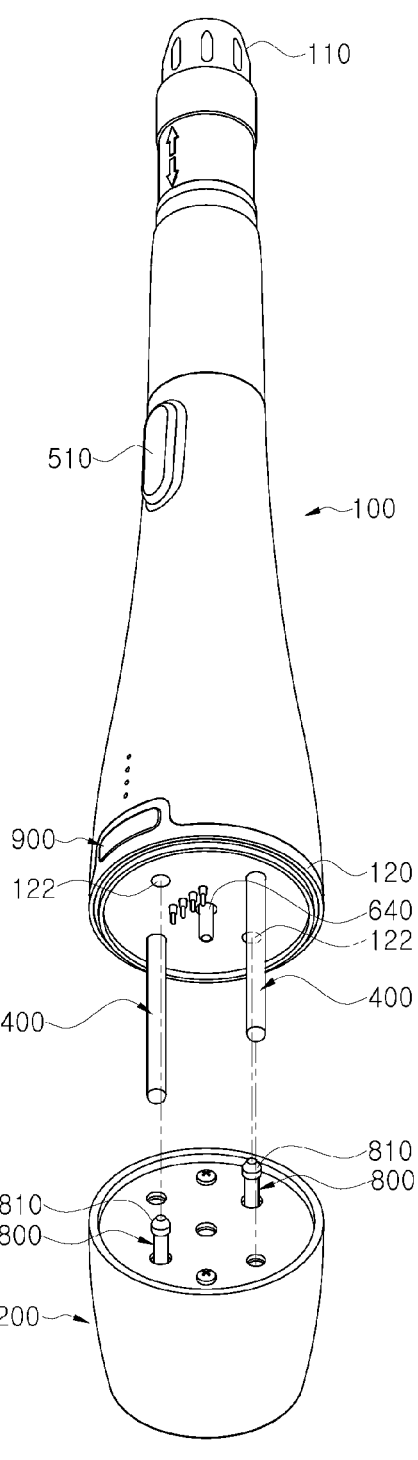
FIG. 2 is a perspective view illustrating a state in which a handpiece and a cartridge housing of the temperature measurement-based ultrasound output device are disassembled from each other according to the embodiment of the present disclosure.
Figure 3:
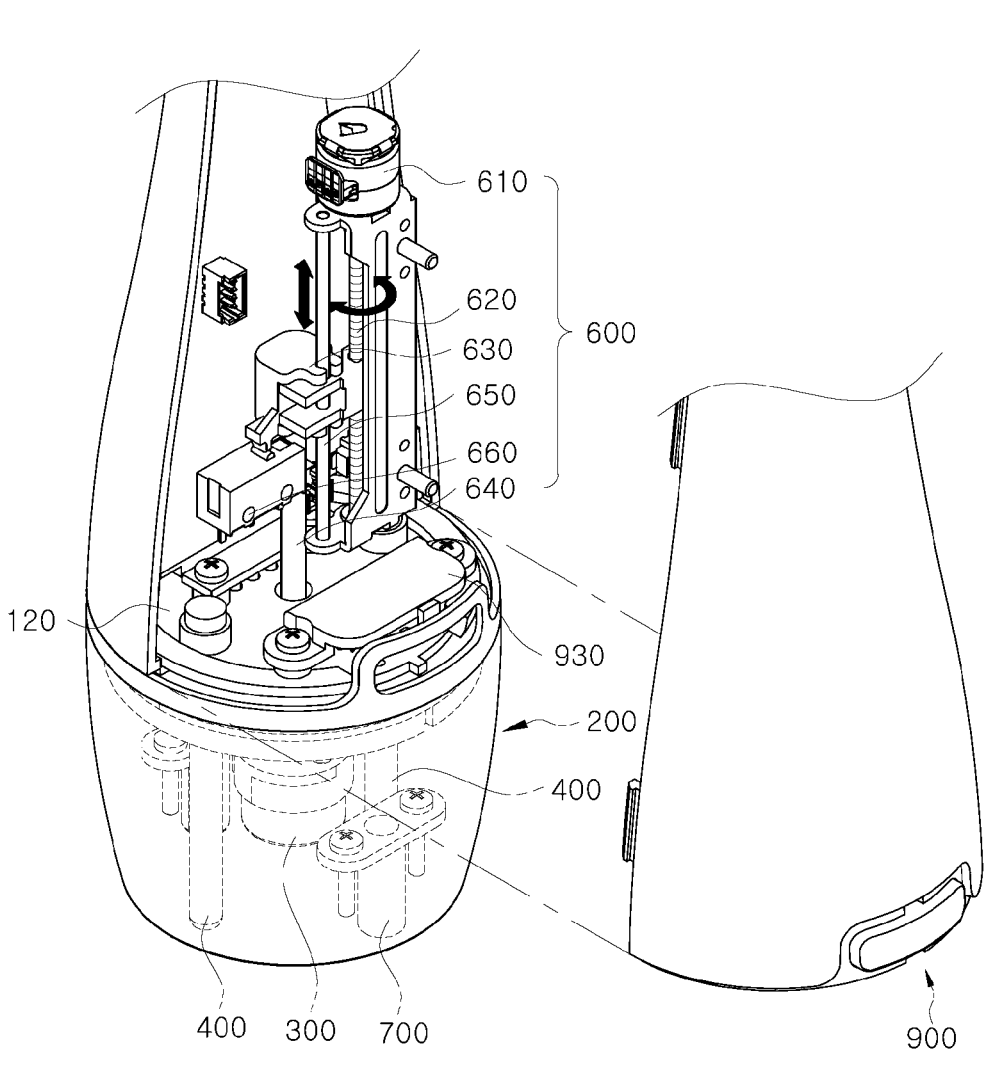
FIG. 3 is a perspective view illustrating a transfer unit of the temperature measurement-based ultrasound output device according to the embodiment of the present disclosure.

FIG. 1 is a perspective view illustrating a temperature measurement-based ultrasound output device according to an embodiment of the present disclosure, FIG. 2 is a perspective view illustrating a state in which a handpiece 100 and a cartridge 200 housing of the temperature measurement-based ultrasound output device are disassembled from each other according to the embodiment of the present disclosure, and FIG. 3 is a perspective view illustrating a transfer unit 600 of the temperature measurement-based ultrasound output device according to the embodiment of the present disclosure.

As illustrated in FIGS. 1 to 3, the temperature measurement-based ultrasound output device according to the embodiment of the present disclosure includes the handpiece 100, the cartridge 200, a transducer 300, a temperature sensor 400, and a controller 500.

The handpiece 100 and cartridge 200, which are basic bodies, may serve as a handle that a user grips.

The cartridge 200 may be detachably coupled to the handpiece 100, and the transducer 300 that outputs ultrasound may be provided in the cartridge 200. Thus, in a state in which the cartridge 200 is in contact with a target part of a skin, while the cartridge 200 moves along the target part of the skin, the ultrasound output from the transducer 300 is focused to a target depth of the skin, and an ultrasound medical procedure may be performed.

In the embodiment, a plug 110 to which a power cable is connected may be provided at one end of the handpiece 100, and the other end of the handpiece 100 may be covered by a bottom cap 120. A connector insertion part 122 to which a connector 800, which will be described below, is detachably coupled may be formed in the bottom cap 120 of the handpiece 100.

In the embodiment, the handpiece 100 may be provided with a circuit board 130 in which power is supplied to the transducer 300 and the controller 500 is provided.

In the embodiment, the handpiece 100 may be provided with the transfer unit 600 that transfers the transducer 300 in a longitudinal direction of the handpiece 100.

The transfer unit 600 may include a driving motor 610, a screw shaft 620, a moving nut 630, a moving shaft 640, a support shaft 650, and a stopper 660.

The driving motor 610 is provided in the handpiece 100 and serves to rotate the screw shaft 620 forward and backward.

The screw shaft 620 is disposed in the longitudinal direction of the handpiece 100 and rotates forward and reverse by the driving motor 610, and the moving nut 630 is screw-coupled to the screw shaft 620.

The moving nut 630 may be screw-coupled to the screw shaft 620 and may reciprocate along the screw shaft 620 when the screw shaft 620 rotates forward or rearward.

The moving shaft 640 may connect the moving nut 630 and the transducer 300 and may move the transducer 300 in conjunction with movement of the moving nut 630. Here, the moving shaft 640 and the transducer 300 may be detachably coupled. For example, the moving shaft 640 and the transducer 300 may be magnetically coupled through a pair of magnetic bodies (not illustrated) provided in the moving shaft 640 and the transducer 300. Further, the moving shaft 640 and the transducer 300 may be screw-coupled. Further, the moving shaft 640 may pass through the bottom cap 120.

The support shaft 650 is provided in the housing, passes through the moving nut 630, and serves to guide the movement of the moving nut 630.

The stopper 660 is provided between the moving nut 630 and the bottom cap 120 and serves to limit movement in a direction in which the moving nut 630 approaches the bottom cap 120 and therefore limit movement in a direction in which the moving shaft 640 and the transducer 300 approach a head part 210 of the cartridge 200.

The cartridge 200, which is a type of housing that accommodates the transducer 300, may have the head part 210 in contact with the target part of the skin. A sensor mounting hole 212, on which the temperature sensor 400 which will be described below is mounted, and an electrode mounting hole 214, on which a high-frequency electrode 700 which will be described below is mounted, may be formed in the head part 210. Further, the head part 210 may be provided with a transparent window 220 through which the ultrasound output from the transducer 300 passes. Here, the transparent window 220 may include a material that transmits the ultrasound. Meanwhile, the head part 210 may be provided on a bottom surface of the cartridge 200.

In the embodiment, one end of the cartridge 200 may be covered by a ceiling cap 230, and the head part 210 may be provided at the other end of the cartridge 200.

The cartridge 200 may contain a fluid medium that transmits the ultrasound generated by the transducer 300. For example, the fluid medium may be at least one of distilled water, degassed liquid, and silicon, but the present disclosure is not particularly limited thereto.

The transducer 300 may be provided in the cartridge 200 to output the ultrasound toward the target part of the skin.

The transducer 300 may reciprocate in the longitudinal direction of the handpiece 100 by the transfer unit 600. Here, the reciprocating of the transducer 300 in the longitudinal direction of the handpiece 100 may mean that, as the transducer 300 moves in a direction approaching the skin or a direction away from the skin, a focus depth of the ultrasound output from the transducer 300 into the target part of the skin increases or decreases.

In the embodiment, the cartridge 200 and the handpiece 100 may be detachably coupled, and for example, the cartridge 200 and the handpiece 100 may be mutually detachably coupled through the connector 800, which will be described below. Thus, in the handpiece 100, the cartridge 200 may be freely replaced and used.

The temperature sensor 400 is provided in the head part 210 and serves to measure a temperature of the target part of the skin. For example, the temperature sensor 400 may be of a contact type that measures a temperature while in contact with a surface of the target part of the skin.

The controller 500 may operate or stop the transducer 300 based on the temperature data measured by the temperature sensor 400. In detail, the controller 500 is electrically connected to the temperature sensor 400, may operate the transducer 300 when the temperature data measured by the temperature sensor 400 is smaller than or equal to a set reference temperature value, and may stop the transducer 300 when the temperature data measured by the temperature sensor 400 is greater than the set reference temperature value.

Here, the reference temperature value set in the controller 500 may increase or decrease depending on the focus depth of the ultrasound focused on the target part of the skin. In this way, the reason why the reference temperature value set in the controller 500 increases or decreases is that an increases in the temperature of the skin, which is measured by the temperature sensor 400, decreases as the focus depth of the ultrasound focused on the target part of the skin increases.

For example, when the ultrasound output from the transducer 300 is focused on the target part of the skin at a depth of 3 mm, when the temperature of the target part of the skin at the depth of 3 mm increases to 56° C. that is a coagulation necrosis temperature, the temperature measured on a surface of the skin by the temperature sensor 400 may be 41° C., and an increase in the temperature of the surface of the skin may be 3° C. Thus, when the ultrasound output from the transducer 300 is focused on the target part of the skin at the depth of 3 mm, the reference temperature value set in the controller 500 may be 41° C.

Further, when the ultrasound output from the transducer 300 is focused on the target part of the skin at a depth of 6 mm, when the temperature of the target part of the skin at the depth of 6 mm increases to 56° C. that is a coagulation necrosis temperature, the temperature measured on the surface of the skin by the temperature sensor 400 may be 40° C., and an increase in the temperature of the surface of the skin may be 2° C. Thus, when the ultrasound output from the transducer 300 is focused on the target part of the skin at the depth of 6 mm, the reference temperature value set in the controller 500 may be 40° C.

In this way, in the present disclosure, while the transducer 300 transmits the ultrasound to the target part of the skin, the controller 500 operates or stops the transducer 300 according to the temperature measured in the target part of the skin by the temperature sensor 400, and thus an appropriate amount of ultrasound may be transmitted to the target part of the skin.

On the other hand, as the same amount of ultrasound is always transmitted to the target part of the skin, the target part of the skin is burned because the amount of ultrasound, which is greater than the appropriate amount, is transmitted, or the coagulation necrosis does not occur in the target part of the skin because the amount of ultrasound, which is smaller than the appropriate amount, is transmitted.

Meanwhile, the reference temperature value set in the controller 500 may be set to a temperature that is safe for skin burns or a temperature that is easy for treatment. Further, the controller 500 may operate the transducer 300 until the temperature data measured on the surface of the skin by the temperature sensor 400 reaches the reference temperature value and may stop the transducer 300 when the temperature data measured on the surface of the skin by the temperature sensor 400 is greater than the reference temperature value.

In the embodiment, the controller 500 may control the transducer 300 to increase or decrease an output intensity and output time of the ultrasound output from the transducer 300 according to the temperature data measured by the temperature sensor 400. For example, the controller 500 may control the transducer 300 to decease the output intensity and output time of the ultrasound output from the transducer 300 when the temperature data measured by the temperature sensor 400 increases. In the embodiment, a plurality of temperature sensors 400 may be provided, and the plurality of temperature sensors 400 may be arranged symmetrical to the head part 210. In other words, the plurality of temperature sensors 400 may be arranged symmetrically with respect to a center of the head part 210. Thus, the plurality of temperature sensors 400 may measure a temperature at a point symmetrical with respect to a center of the target part of the skin that is in contact with the center of the head part 210. Furthermore, the controller 500 may calculate an average value of the temperature data measured by the plurality of temperature sensors 400, may operate the transducer 300 when the average value is smaller than or equal to the set reference temperature value, and may stop the transducer 300 when the average value is greater than the set reference temperature value.

Meanwhile, the controller 500 may further include an adjustment button 510 that receives an operation direction of the transfer unit 600 so that the transducer 300 is transferred in a direction approaching the skin or away from the skin.

The adjustment button 510 may be provided on an outer surface of the handpiece 100. For example, the controller

500 may control the operation direction of the transfer unit 600 so that the transducer 300 transfers in the direction approaching the skin when a lower portion of the adjustment button 510 is pushed. Further, the controller 500 may control the operation direction of the transfer unit 600 so that the transducer 300 transfers in the direction away from the skin when an upper portion of the adjustment button 510 is pushed.

Figure 4:
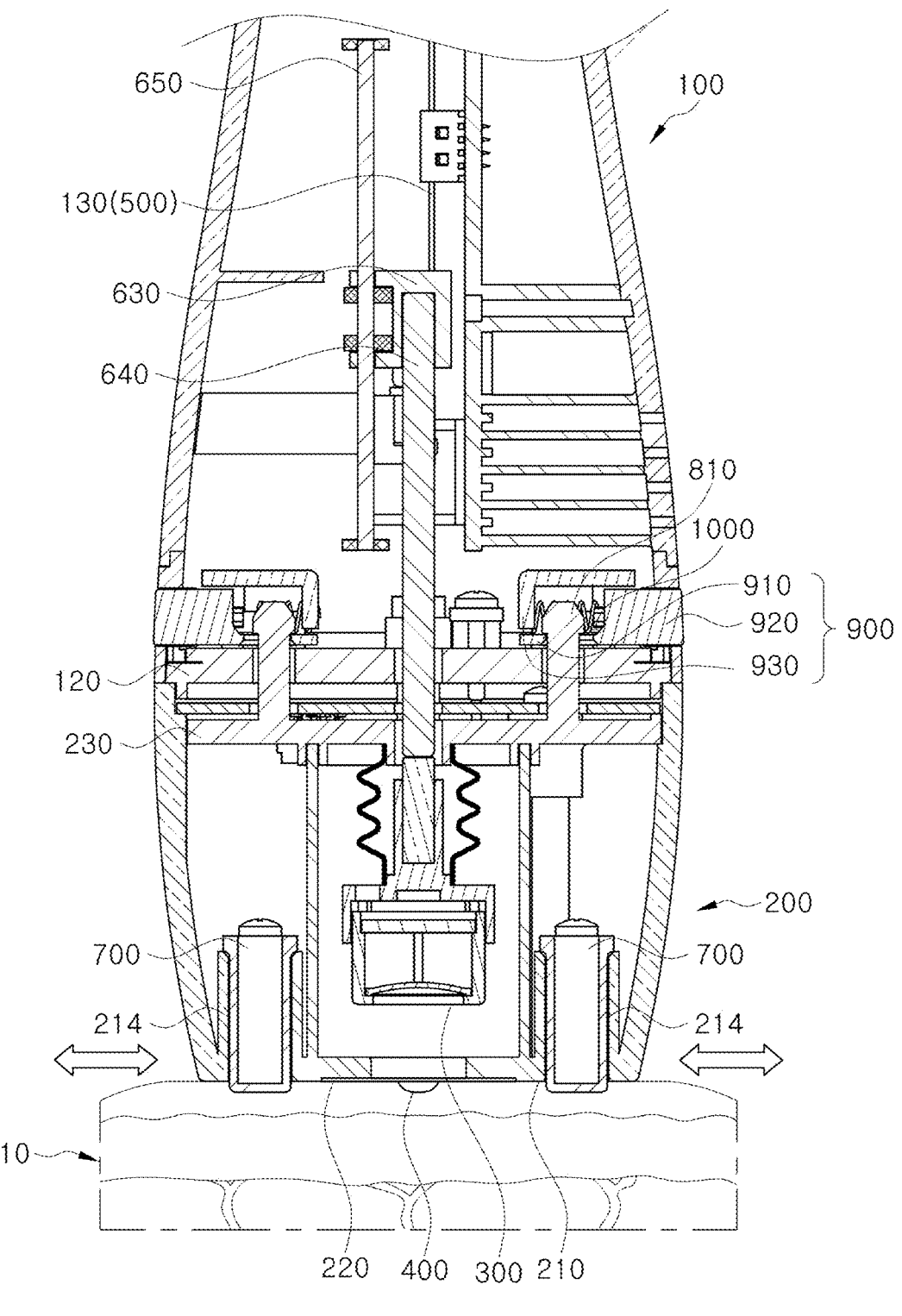
FIG. 4 is a cross-sectional view along line A-A' of FIG. 1.
Figure 5:
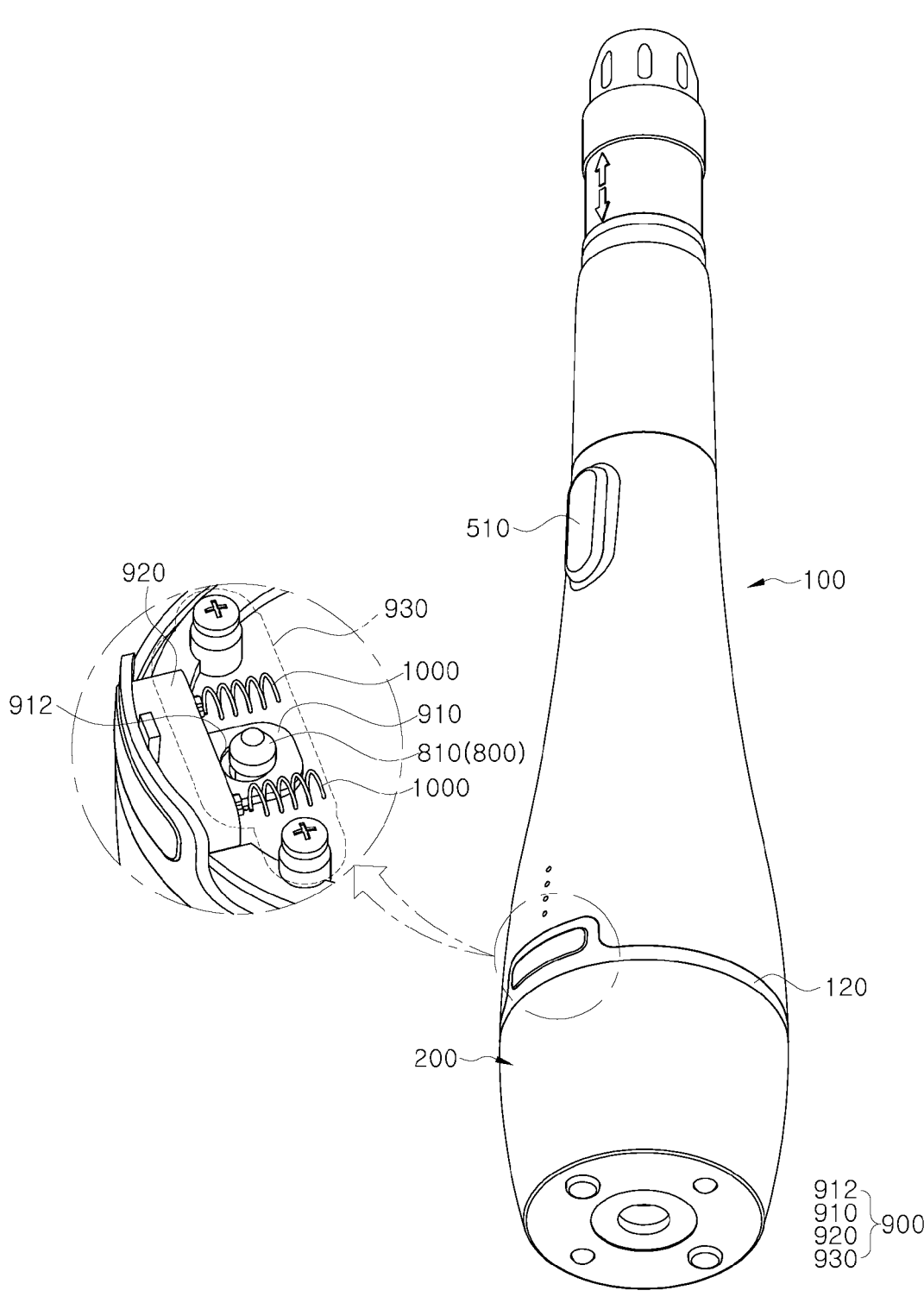
FIG. 5 is a perspective view illustrating a state in which the handpiece and the cartridge housing are coupled to each other through a connector and a knob of the temperature measurement-based ultrasound output device according to the embodiment of the present disclosure.
Figure 6:
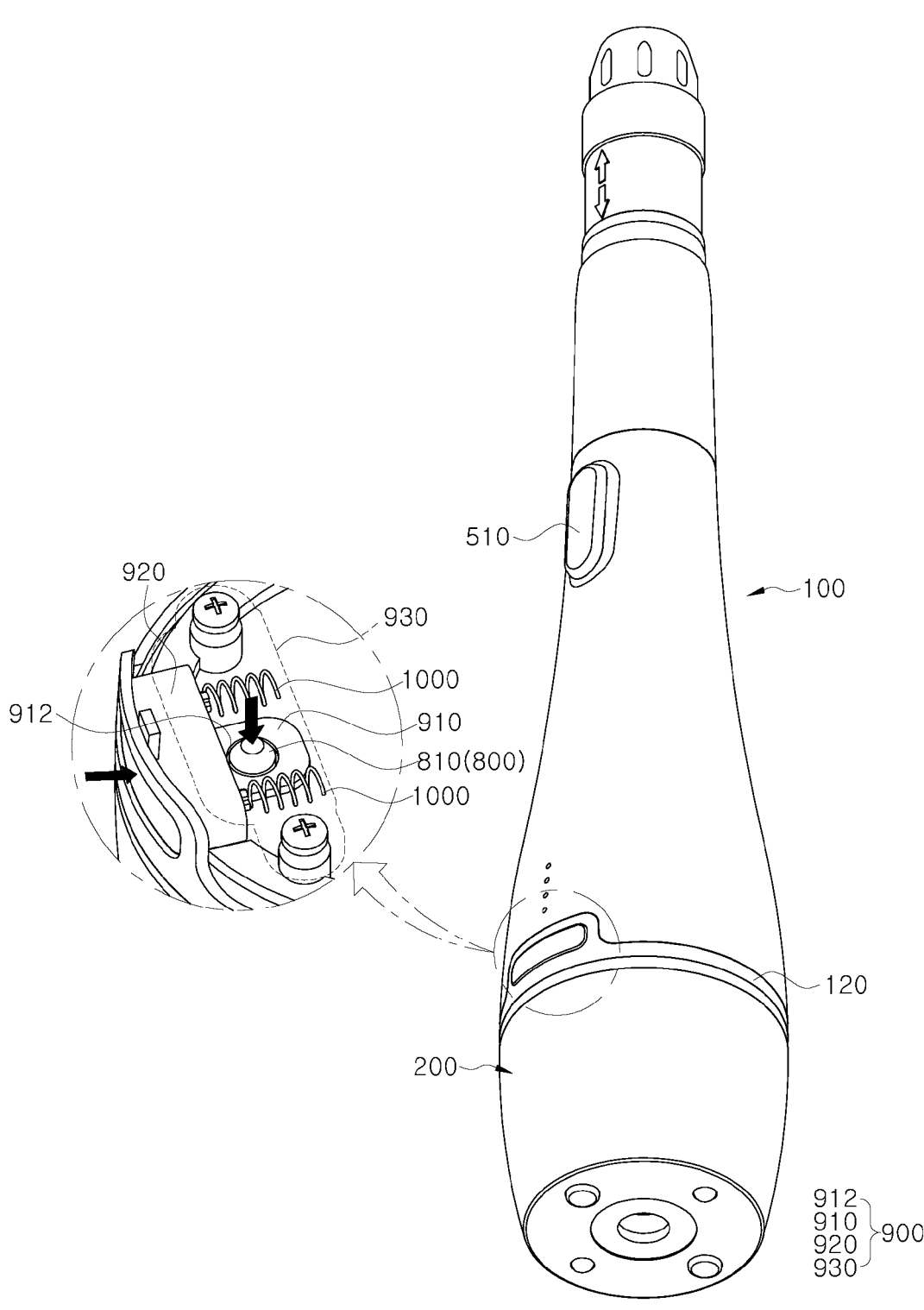
FIG. 6 is a perspective view illustrating a state in which the handpiece and the cartridge housing are uncoupled from each other through the connector and the knob of the temperature measurement-based ultrasound output device according to the embodiment of the present disclosure.
Figure 7:
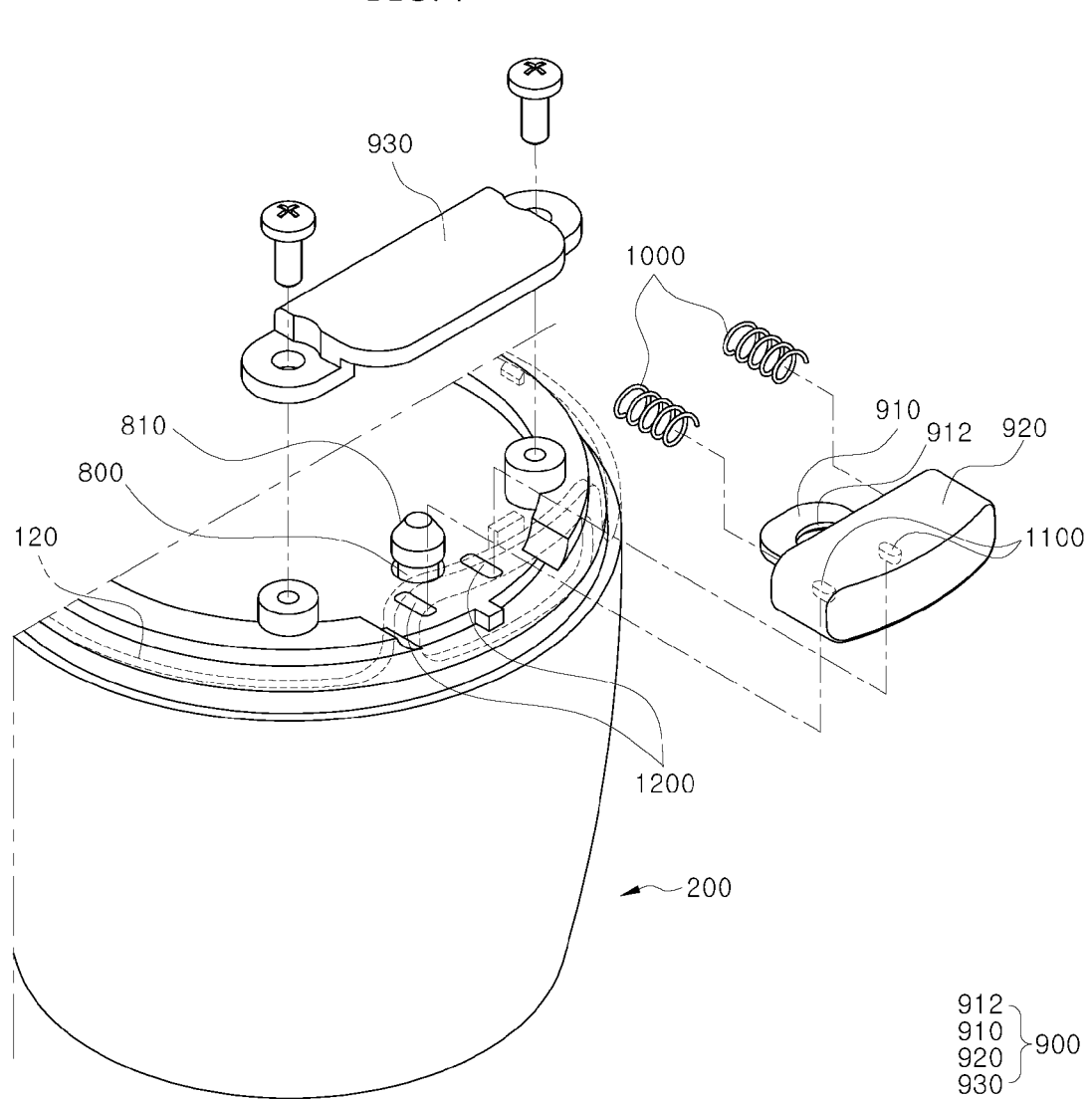
FIG. 7 is an exploded perspective view illustrating the connector, the knob, and an elastic member of the temperature measurement-based ultrasound output device according to the embodiment of the present disclosure.

FIG. 4 is a cross-sectional view along line A-A' of FIG. 1, FIG. 5 is a perspective view illustrating a state in which the handpiece 100 and the cartridge 200 housing are coupled to each other through the connector 800 and a knob 900 of the temperature measurement-based ultrasound output device according to the embodiment of the present disclosure, FIG. 6 is a perspective view illustrating a state in which the handpiece 100 and the cartridge 200 housing are uncoupled from each other through the connector 800 and the knob 900 of the temperature measurement-based ultrasound output device according to the embodiment of the present disclosure, and FIG. 7 is an exploded perspective view illustrating the connector 800, the knob 900, and an elastic member 1000 of the temperature measurement-based ultrasound output device according to the embodiment of the present disclosure.

As illustrated in FIGS. 1 to 7, the temperature measurement-based ultrasound output device according to the embodiment of the present disclosure may further include the high-frequency electrode 700, the connector 800, the knob 900, the elastic member 1000, a guide protrusion 1100, and a guide groove 1200.

The high-frequency electrode 700 may be provided in the head part 210, may provide electrical energy to the target part of the skin, and may measure an impedance of the target part of the skin. In this case, the controller 500 may operate the transducer 300 when the impedance data, which is measured by the high-frequency electrode 700, is smaller than or equal to a set reference impedance value and may stop the transducer 300 when the impedance data is greater than the set reference impedance value.

Meanwhile, the reference impedance value set in the controller 500 may be set to a temperature that is safe for skin burns or a temperature that is easy for treatment. Further, the controller 500 may operate the transducer 300 until the impedance data, which is measured by the high-frequency electrode 700, reaches a reference impedance value, and then may stop the transducer 300 when the impedance data, which is measured by the high-frequency electrode 700, is greater than or equal to the reference impedance value.

In the embodiment, the controller 500 may control the transducer 300 to increase or decrease the output intensity and output time of the ultrasound output from the transducer 300 according to the impedance data measured by the high-frequency electrode 700. For example, the controller 500 may control the transducer 300 to decease the output intensity and output time of the ultrasound output from the transducer 300 when the impedance data measured by the high-frequency electrode 700 increases.

In the embodiment, a plurality of high-frequency electrodes 700 may be provided, and the plurality of high-frequency electrodes 700 may be arranged symmetrically to the head part 210. The plurality of high-frequency electrodes 700 may be of a bipolar type including a positive-pole needle and a negative-pole needle. In this bipolar type, a current applied to the positive-pole needle may be fed back to the negative-pole needle. As a result, an energy transfer area through which electrical energy is transmitted may be formed between the positive-pole needle and the negative-pole needle.

The connector 800 may protrude from the cartridge 200 toward the handpiece 100. The connector 800 serves to detachably couple the cartridge 200 and the handpiece 100. The connector 800 may be detachably coupled to the connector insertion part 122 provided on the bottom cap 120 of the handpiece 100.

The knob 900, which supports the connector 800 and is movably provided in the handpiece 100, may allow the connector 800 to reciprocate such that the connector 800 is positioned at a locked position in which the connector 800 is locked to the connector insertion part 122 or an unlocked position in which the connector 800 is unlocked from the connector insertion part 122.

The knob 900 may include a movement member 910 and an operation member 920.

The movement member 910 has a through-hole 912 through which the connector 800 is inserted and supported, and may move between the locked position and the unlocked position. Here, a step 810 through which the through-hole 912 of the movement member 910 is fixedly locked or unlocked may be formed at a distal end of the connector 800. In detail, when the movement member 910 is moved to the locked position, the step 810 of the connector 800 is fixedly locked by the through-hole 912 of the movement member 910, and thus the connector 800 may be locked by the connector insertion part 122. Further, when the movement member 910 is moved to the unlocked position, the step 810 of the connector 800 is fixedly unlocked from the through-hole 912 of the movement member 910, and thus the connector 800 may be unlocked from the connector insertion part 122. In this case, the step 810 of the connector 800 may pass through the through-hole 912 of the movement member 910 and may be separated from the through-hole 912 of the movement member 910 and the connector insertion part 122 of the handpiece 100.

The operation member 920 is connected to the movement member 910, is exposed to the outside of the handpiece 100, and serves to perform operation so that the movement member 910 moves between the locked position and the unlocked position. For example, the operation member 920 may have the form of a button that is operated to move the movement member 910 to the unlocked position by pushing by the user.

The operation member 920 may be supported by a cover 930 coupled to the bottom cap 120 of the handpiece 100.

The elastic member 1000 may generate an elastic force on the knob 900 so that the connector 800 is positioned in the locked position. The elastic member 1000 may be elastically supported between the cover 930 and the operation member 920.

The guide protrusion 1100 may be provided in the knob 900. The guide protrusion 1100 may have a shape that protrudes from the knob 900 toward the guide groove 1200, which will be described below.

The guide groove 1200 may be provided on the bottom cap 120 of the handpiece 100 so that the guide protrusion 1100 may reciprocate and may guide the knob 900 so that the knob 900 reciprocates between the locked position and the unlocked position.

An operation process of outputting the ultrasound to the skin by the temperature measurement-based ultrasound output device according to the embodiment of the present disclosure will be described.

9

Figure 8:
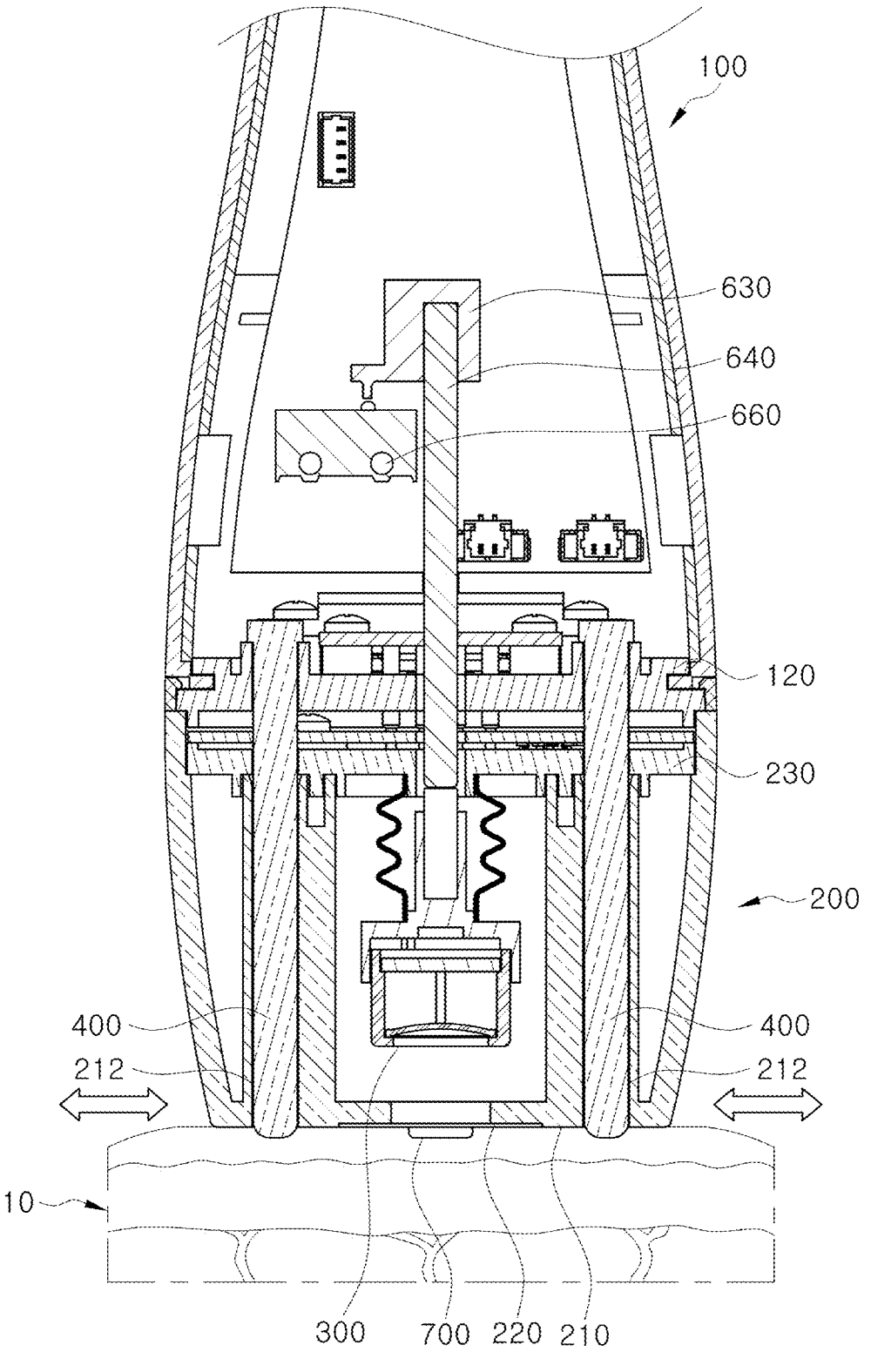
FIG. 8 is a cross-sectional view illustrating a state in which the temperature measurement-based ultrasound output device outputs ultrasound to a skin according to the embodiment of the present disclosure, based on a cross section along line B-B' of FIG. 1.

FIG. 8 is a cross-sectional view illustrating a state in which the temperature measurement-based ultrasound output device outputs ultrasound to a skin according to the embodiment of the present disclosure, based on a cross section along line B-B' of FIG. 1. The following process may be performed by the controller 500 or the user.

As illustrated in FIG. 8, the handpiece 100 and cartridge 200 move along a target part of a skin 10. In this case, the transducer 300 focuses the ultrasound onto the target part of the skin 10, and the temperature sensor 400 measures the temperature of the surface of the target part of the skin.

Next, the controller 500 operates the transducer 300 when the temperature data measured by the temperature sensor 400 is smaller than or equal to the set reference temperature value and stops the transducer 300 when the temperature data measured by the temperature sensor 400 is greater than the set reference temperature value.

Thus, in the temperature measurement-based ultrasound output device according to the embodiment of the present disclosure, while the transducer transmits the ultrasound to the target part of the skin, the transducer is operated or stopped according to the temperature data measured in the target part of the skin, and thus an appropriate amount of ultrasound may be transmitted to the target part of the skin.

Hereinabove, embodiments of the present disclosure have been described with reference to the to the accompanying drawings. However, those skilled in the art to which the present disclosure pertains can understand that the present disclosure can be implemented in other specific forms without changing the technical spirit or essential features thereof. Therefore, it should be understood that the embodiments described above are illustrative but not limiting in all aspects.

What is claimed is:

1. A temperature measurement-based ultrasound output device comprising:

a cartridge having a head part configured to be in contact with a target part of a skin;

a handpiece detachably coupled to the cartridge, wherein the handpiece has an elongated shape having a first distal end and a second distal end, wherein the first distal end of the handpiece is coupled with the cartridge;

a transducer provided in the cartridge, and configured to output ultrasound toward the target part;

a temperature sensor provided in the head part, and configured to measure a temperature at the target part;

a controller configured to:

set a reference temperature value, based on a focus depth of the ultrasound focused on the target part;

control the transducer to decrease an output intensity and an output time of the ultrasound when the temperature measured by the temperature sensor is smaller than or equal to the reference temperature value and is increasing;

control the transducer to increase the output intensity and the output time of the ultrasound when the temperature measured by the temperature sensor is smaller than or equal to the reference temperature value and is decreasing;

control the transducer to stop outputting the ultrasound when the temperature measured by the temperature sensor is greater than the reference temperature value; and a transfer unit configured to move the transducer along with a straight direction from the first distal end and the second distal end of the handpiece,

wherein the transfer unit comprises:

a screw shaft disposed along with the straight direction from the first distal end and the second distal end of the handpiece;

a moving nut screw-coupled to the screw shaft;

a moving shaft configured to connect the moving nut and the transducer;

a driving motor configured to rotate the screw shaft forward or rearward such that the moving nut moves along with the straight direction from the first distal end and the second distal end of the handpiece; and a stopper provided between the moving nut and the cartridge, and configured to limit a movement range in a direction in which the moving nut approaches the cartridge to limit a movement range in a direction in which the transducer approaches the head part.

2. The temperature measurement-based ultrasound output device of claim 1, further comprising:

an electrode provided in the head part, configured to provide electrical energy to the target part, and configured to measure an impedance at the target part, wherein the controller is further configured to:

set a reference impedance value;

control the transducer to decrease the output intensity and the output time of the ultrasound when the impedance measured by the electrode is smaller than or equal to the reference impedance value and is increasing;

control the transducer to increase the output intensity and the output time of the ultrasound when the impedance measured by the electrode is smaller than or equal to the reference impedance value and is decreasing; and control the transducer to stop outputting the ultrasound when the impedance measured by the electrode is greater than the reference impedance value.

3. The temperature measurement-based ultrasound output device of claim 2, wherein the electrode is provided in plurality, and the plurality of electrodes are symmetrically arranged in the head part.

4. The temperature measurement-based ultrasound output device of claim 1, further comprising:

a connector protruding from the cartridge toward the handpiece; and a connector insertion part which is provided in the handpiece and to which the connector is detachably coupled.

5. The temperature measurement-based ultrasound output device of claim 4, further comprising:

a knob configured to support the connector, provided to be movable on the handpiece, and configured to reciprocate the connector such that the connector is positioned at a locking position in which the connector is locked to the connector insertion part or an unlocking position in which the connector is unlocked from the connector insertion part.

6. The temperature measurement-based ultrasound output device of claim 5, further comprising:

an elastic member configured to generate an elastic force on the knob such that the connector is positioned at the locking position.

7. The temperature measurement-based ultrasound output device of claim 6, further comprising:

a guide protrusion provided in the knob; and a guide groove provided in the handpiece such that the guide protrusion reciprocates and configured to guide the knob such that the knob reciprocates between the locked position and the unlocked position.

8. The temperature measurement-based ultrasound output device of claim 1, wherein the second distal end of the handpiece has a plug.

9. A temperature measurement-based ultrasound output device comprising:

a cartridge having a head part configured to be in contact with a target part of a skin;

a handpiece detachably coupled to the cartridge, wherein the handpiece has an elongated shape having a first distal end and a second distal end, wherein the first distal end of the handpiece is coupled with the cartridge;

a transducer provided in the cartridge, and configured to output ultrasound toward the target part;

a plurality of temperature sensors, which are symmetrically arranged in the head part, and configured to measure a temperature at the target part;

a controller configured to:

set a reference temperature value, based on a focus depth of the ultrasound focused on the target part;

calculate an average value of temperature data measured by the plurality of temperature sensors;

control the transducer to decrease an output intensity and an output time of the ultrasound when the average value is smaller than or equal to the reference temperature value and is increasing;

control the transducer to increase the output intensity and the output time of the ultrasound when the average value is smaller than or equal to the reference temperature value and is decreasing;

control the transducer to stop outputting the ultrasound when the average value is greater than the reference temperature value; and a transfer unit configured to move the transducer along with a straight direction from the first distal end and the second distal end of the handpiece, wherein the transfer unit comprises:

a screw shaft disposed along with the straight direction from the first distal end and the second distal end of the handpiece;

a moving nut screw-coupled to the screw shaft;

a moving shaft configured to connect the moving nut and the transducer;

a driving motor configured to rotate the screw shaft forward or rearward such that the moving nut moves along with the straight direction from the first distal end and the second distal end of the handpiece; and a stopper provided between the moving nut and the cartridge, and configured to limit a movement range in a direction in which the moving nut approaches the cartridge to limit a movement range in a direction in which the transducer approaches the head part.

10. The temperature measurement-based ultrasound output device of claim 9, further comprising:

an electrode provided in the head part, configured to provide electrical energy to the target part, and configured to measure an impedance of the target part, wherein the controller is further configured to:

set a reference impedance value;

control the transducer to decrease the output intensity and the output time of the ultrasound when the impedance measured by the electrode is smaller than or equal to the reference impedance value and is increasing;

control the transducer to increase the output intensity and the output time of the ultrasound when the impedance measured by the electrode is smaller than or equal to the reference impedance value and is decreasing; and control the transducer to stop outputting the ultrasound when the impedance measured by the electrode is greater than the reference impedance value.

11. The temperature measurement-based ultrasound output device of claim 10, wherein the electrode is provided in plurality, and the plurality of electrodes are symmetrically arranged in the head part.

12. The temperature measurement-based ultrasound output device of claim 9, further comprising:

a connector protruding from the cartridge toward the handpiece; and a connector insertion part which is provided in the handpiece and to which the connector is detachably coupled.

13. The temperature measurement-based ultrasound output device of claim 12, further comprising:

a knob configured to support the connector, provided to be movable on the handpiece, and configured to reciprocate the connector such that the connector is positioned at a locking position in which the connector is locked to the connector insertion part or an unlocking position in which the connector is unlocked from the connector insertion part.

14. The temperature measurement-based ultrasound output device of claim 13, further comprising:

an elastic member configured to generate an elastic force on the knob such that the connector is positioned at the locking position.

15. The temperature measurement-based ultrasound output device of claim 14, further comprising:

a guide protrusion provided in the knob; and a guide groove provided in the handpiece such that the guide protrusion reciprocates and configured to guide the knob such that the knob reciprocates between the locked position and the unlocked position.

\* \* \* \* \*